United States Patent [19]

Milosevic et al.

[11] Patent Number: 5,048,970
[45] Date of Patent: Sep. 17, 1991

[54] OPTICAL ATTACHMENT FOR VARIABLE ANGLE REFLECTION SPECTROSCOPY

[75] Inventors: Milan Milosevic, Fishkill, N.Y.; Nicolas J. Harrick, Croton Dam Rd., Ossining, N.Y. 10562

[73] Assignee: Nicolas J. Harrick, Ossining, N.Y.

[21] Appl. No.: 546,081

[22] Filed: Jun. 29, 1990

[51] Int. Cl.$^5$ .............................................. G01N 21/01
[52] U.S. Cl. ..................................... 356/445; 356/244
[58] Field of Search ................ 356/346, 244, 445, 446

[56] References Cited

U.S. PATENT DOCUMENTS

| | | | |
|---|---|---|---|
| 4,473,295 | 9/1984 | Doyle | 356/244 |
| 4,479,058 | 10/1984 | Gast et al. | 356/244 |
| 4,657,390 | 4/1987 | Doyle | 356/244 |
| 4,692,024 | 9/1987 | Bloss | 356/135 |
| 4,853,542 | 8/1989 | Milosevic et al. | 356/446 |

FOREIGN PATENT DOCUMENTS

| | | | |
|---|---|---|---|
| 47-39911 | 9/1972 | Japan | 356/445 |
| 60-244823 | 12/1985 | Japan | 356/346 |

OTHER PUBLICATIONS

Brimmer et al., "Angular Dependence of Diffuse Reflectance Infrared Spectra. Part I: FT-IR Spectrogoniophotometer", Applied Spectroscopy, vol. 40, #2, 1986, pp. 258-265.
Harrick Scientific Co., "Reflection Attachment", Applied Spectroscopy, vol. 44, #2, 2/90, p. 36a.

*Primary Examiner*—F. L. Evans
*Assistant Examiner*—K. P. Hantis

[57] ABSTRACT

A vaariable angle reflection accessory for use in reflection spectrometry characterized by a pair of fixed ellipsoidal reflectors positioned over the sample surface and a pair of rotatable plane mirrors positions at opposite sides of the sample surface. The spectrometer beam is brought to a focus at the first plane mirror, from which it is reflected off the first ellipsoidal reflector to a focus at the sample surface. The reflected beam follows a corresponding path back to the spectrometer. Rotating the mirrors in unison causes the beam angle of incidence on the sample surface to vary over a wide range while maintaining optical alignments and continuing to center the radiation on the same sample area.

16 Claims, 8 Drawing Sheets

OPTICAL ATTACHMENT FOR VARIABLE ANGLE REFLECTION SPECTROSCOPY

This invention relates to variable angle reflection spectroscopy, and in particular to an accessory for use therein.

BACKGROUND OF THE INVENTION

Variable angle reflectance is an important spectroscopic technique. Certain samples, such as opaque substances, films on opaque substrates, and films on liquids, are tedious or practically impossible to analyze with conventional transmission spectroscopy equipment. The analyses of such samples by reflection spectroscopy, however, are straightforward.

There are three different methods of reflection spectroscopy. The technique employed depends on the nature of the sample and the information sought. External reflection spectroscopy is applicable to thin films on opaque substrates and opaque smooth solids. Internal reflectance permits spectral measurements of liquids, powders, pastes, gels, and soft solids. Diffuse reflectance is most commonly used for the analysis of powders and rough surface solids. Variable angle studies, using either external or internal reflection spectroscopy, provide data for the determination of optical constants and sample thicknesses.

The spectrometer accessories currently available generally perform only one of the three reflection techniques. Furthermore, most variable angle accessories are only useable over a limited range of angles. They also do not maintain alignment and do not reflect the incident radiation from the same sample area when the incident angle is changed. For further backgound on the state of the art of this technology, reference is had to U.S. Pat. No. 3,603,690, and the Harrick Scientific Corporation catalog HSC-831 which describes a number of the currently available reflection accessories.

SUMMARY OF THE INVENTION

An object of the invention is a variable angle reflection attachment that is easily adapted for all three reflection techniques.

A further object of the invention is a variable angle reflection attachment that can be operated over a broad range of incident angles, while maintaining alignment and continuing to center the incident radiation on the same sample area.

These and other objects and advantages as will appear hereinafter are achieved by an accessory for holding the specimen to be analyzed and adapted to be placed in the sampling compartment of a conventional spectrometer. In accordance with a feature of the invention, optical means for directing the radiation beam from the spectrometer onto the specimen includes, in the optical path before the specimen, a first rotatable plane mirror, a first fixed ellipsoidal reflector, and, in the optical path after the specimen, a second fixed ellipsoidal reflector and a second rotatable plane mirror. The two rotatable mirrors are coupled together and rotate equal amounts but in opposite directions. By rotating the coupled plane mirrors, the angle of incidence of the beam on the specimen can be varied over a very wide angle. In addition, the beam can be maintained centered on the specimen while maintaining the focusing and alignment conditions of the spectrometer.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

DETAILED DESCRIPTION OF THE PREFERRED EMBODIMENTS

Any of many conventional spectrometers can be employed with the variable angle reflection accessory of the invention. The conventional spectrometer contains a sampling compartment for receiving the specimen to be analyzed together with suitable optics components for directing the radiation beam emanating from a port of the spectrometer to the accessory and re-directing the beam after interaction with the specimen back into the spectrometer for detection and processing of the resultant electronics signals.

The typical spectrometer beam converges to a point more or less at the center of the sampling compartment and from that point diverges until it reenters the spectrometer. Ideally, one wants to maintain this focussing condition even though an accessory may be present which extends the optical beam path.

Figure 1:
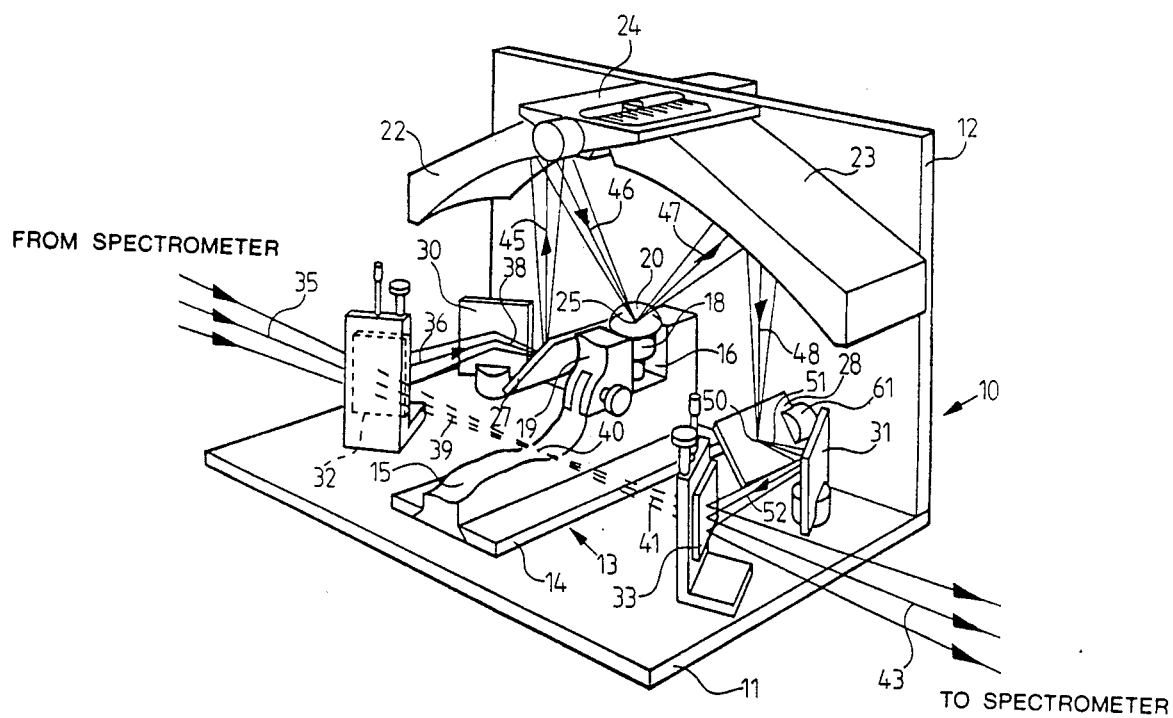
FIG. 1 is a perspective of one form of variable angle reflection accessory in accordance with the invention.

FIG. 1 illustrates one form of accessory of the invention which not only maintains the focussing conditions but in addition maintains the beam alignment, with the result that the optical paths within the spectrometer require no changes. The accessory comprises a stand 10 on which the optical components and sample support are mounted. The stand 10 comprises a base member 11 which simply rests on the surface of the sampling compartment, and a vertical wall member 12. At the center of the base 11 is provided the specimen support 13, which comprises a base 14 having an upstanding support 15 provided with a recessed area 16 onto which the specimen is provided. In this instance, a sampling cup 18 is supported in the recess by a movable jaw 19. The sample 20 of the material to be analyzed is placed in the cup 18. First and second ellipsoidal mirror segments 22, 23 are mounted 24 on the wall 12. The ellipsoidal mirrors 22, 23 are located over the sample 20 to the left and to the right of the latter, and are positioned to have a common focal point 25 at the center of the surface of the specimen 20. Two rotatable mirrors 27, 28 are mounted also on the wall 12 at opposite sides of the sample support 13. The mechanism for rotating them in unison is located on the back side of the wall 12, and is not visible in FIG. 1. Two plane mirrors 30, 31 are mounted on the accessory base 11, again at opposite sides of the sample support 13, and two additional plane mirrors 32, 33 are also mounted on the accessory base 11 on opposite sides of the sample support 13. The mirror 32 is on the back side of its mounting, and is shown in dashed lines.

The converging beam 35 from the spectrometer is incident on the plane mirror 32, from which it is reflected 36, still converging, to the plane mirror 30, and then 38 to the first movable mirror 27. The dashed line ray extensions 39 of the original beam 35 show the beam path had the accessory not been present. As will be noted, the undeflected beam 39 would focus to a point at 40, and then diverge at 41, and again without the accessory present would continue, as shown at 43 in solid lines, back into the spectrometer. The positions of the plane mirrors 32, 30, and 27 are chosen such that the optical path remains the same so that reflected beam 36, 38 also focusses to a point (not shown) at approximately the center of the first movable mirror 27. That latter point is also a focus of the ellipsoidal mirror 22. Therefore, the beam 45 reflected from the first movable mirror 27 onto the surface of the first ellipsoidal mirror 22 will upon reflection 46 be reimaged from the latter at the focal point 25 at the specimen.

The optical path of the beam after interaction with the specimen 20 is similar. Thus, the beam 47 from the specimen upon reflection 48 from the second ellipsoidal mirror 23 is re-focussed at a point 50 approximately at the center of the second movable mirror 28. From there, the reflected beam 51 reflects off of the mirror 31, and from there the beam 52 is reflected from the mirror 33 and is now back in the same optical path 43 to the spectrometer that the beam would have had in the absence of the accessory. The post-specimen optical path 51 and 52 has the same optical length as the pre-specimen optical path 36, 38.

The function of the first ellipsoidal mirror 22 is to refocus the beam from the first movable mirror 27 to the sampling position 25, and the second ellipsoidal mirror 23 collects the radiation reflected from the sample and refocuses it at the second movable mirror 28.

Figure 2A:
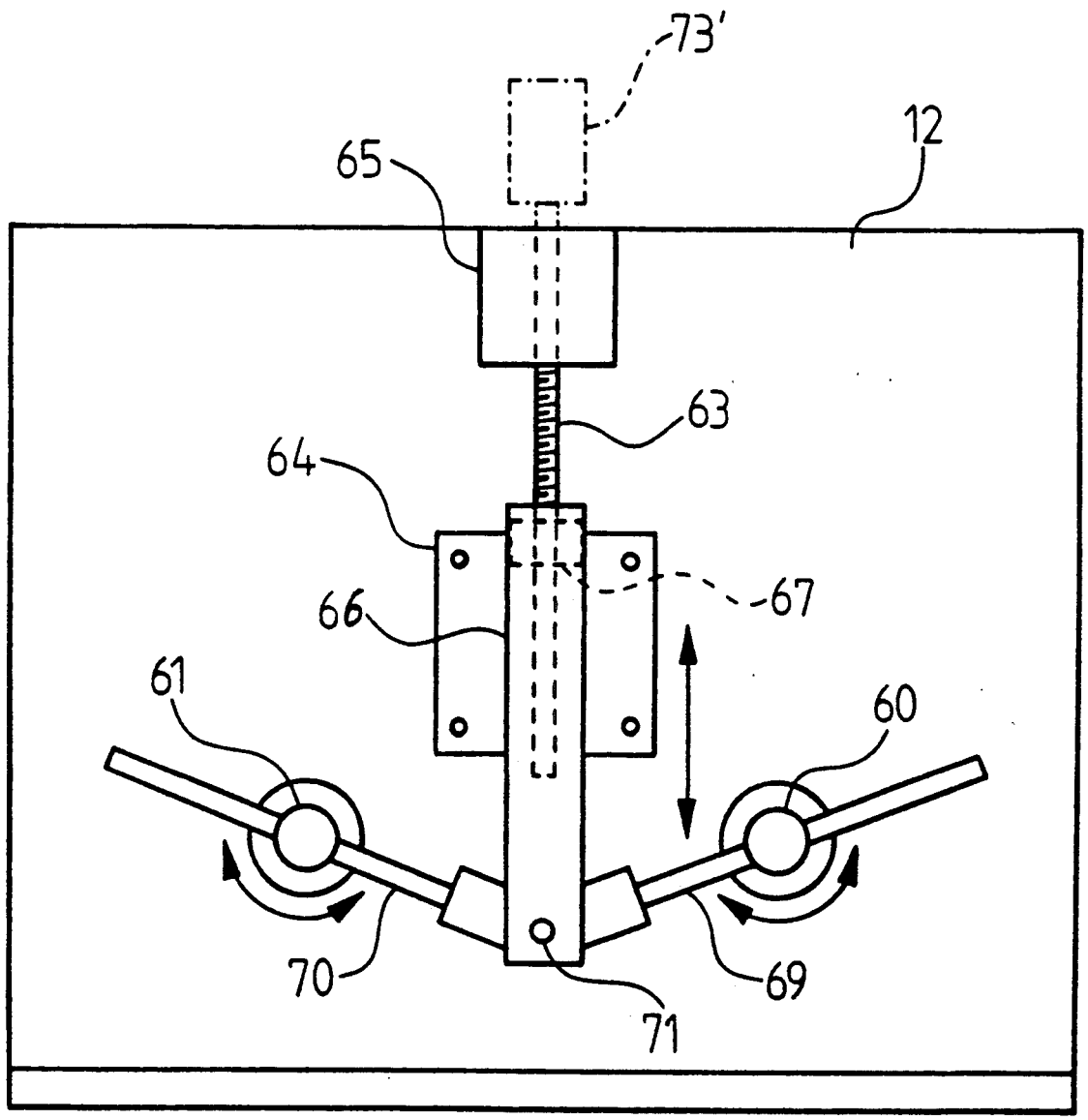
FIGS. 2A and 2B illustrate a suitable mechanism for rotating the plane mirrors in unison.
Figure 2B:
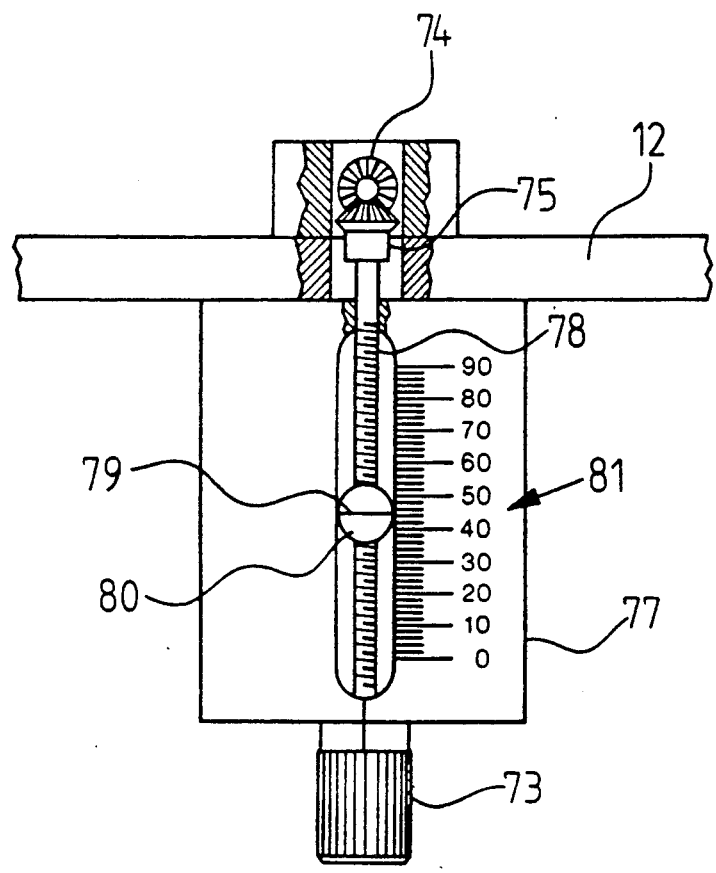

FIGS. 2A and 2B are, respectively, a view of the back and of the top of the accessory support wall 12 showing the mechanism which couples the mirrors 27, 28 to rotate together, in mirror image fashion. The mechanism comprises rotatable supports 60, 61 for the two mirror 27, 28. A lead screw 63 is mounted on journal supports 64, 65. A vertically movable carriage 66 carries a nut 67 that is engaged by the lead screw and causes the carriage 66 to vertically move as the lead screw 63 is rotated. Rods or shafts 69, 70 are pivotably mounted at a common pivot pin 71 on the carriage 66. The movable mirror supports 60, 61 have through-holes through which the shafts 69, 70 freely pass and thus allows the distance between the pivot pin 71 and the rotatable mirror mounts 60, 61 to vary as the carriage moves up and down. This connection is referred to as a floating connection. By providing that the carriage 66 moves exactly along the center line between the two mirror mounts 60, 61, the angles that the two shafts form with the carriage are always equal. By extending the lead screw 63 through the upper support 65, as shown in dash-dot lines, and adding a knob 73', rotation of the knob will provide symmetric, mirror image rotation of the two mirrors.

It is preferred, however, to provide to the user an indication of the angle of incidence. This is accomplished by providing a bevel gear 74 connected to the top of the lead screw 63 and a matching bevel gear 75 journalled at the top of the support (see FIG. 2B), providing a right-angle drive, and then providing a horizontal shelf 77 supporting a second lead screw 78 connected at its end to a knob 73. A threaded nut 79 on the lead screw 78 carries a pointer 80 to a scale 81 displaying various angles of incidence. Rotation of the knob 73 will produce the same effect as before, now with the incident angle indication for the user.

It will be evident from the foregoing description that it is desirable from the user's standpoint that a certain rotation or revolution of the knob 73 will produce the same change in the angle of incidence over the full range of variable angles, i.e., 5°–85°, using a linear scale 81. The advantage would be that the user could then easily interpolate angle positions from the angle positions displayed on the scale, and a vernier indicator could easily be added to the pointer for even finer adjustments. It turns out that, even though the mechanism specifically described in FIGS. 2A and 2B has both linear components as well as non-linear components, the latter can be compensated, so that this desired result of a linear scale with a linear knob rotation is readily achieved by appropriate adjustment of the position of the carriage 66 relative to the shafts 69, 70 at the low or starting end of the range of variable angles available.

Figure 3:
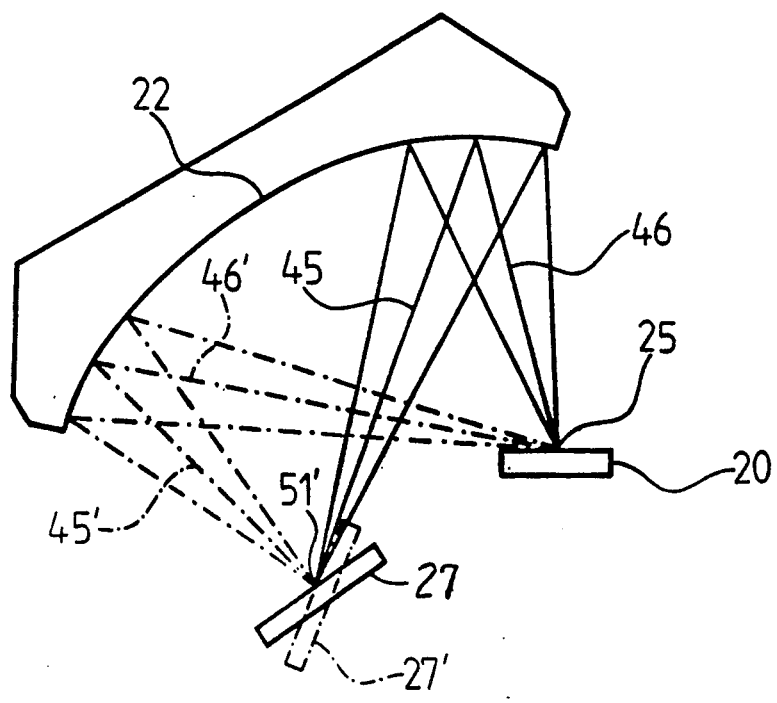
FIG. 3 is a schematic optics diagram illustrating operation of the accessory of the invention.

When the knob 73 is thus rotated, it causes the beam 45 to scan over the length of the ellipsoidal segment 22. The result is to cause the reflected beam 46 angle of incidence on the specimen 20 to vary. FIG. 3 is a sketch of the optical path showing this feature. The first movable mirror 27 is shown in solid lines in a first position 27 and in dashed lines in a second position 27'. The first fixed ellipsoidal segment 22, and the specimen 25 are also shown. In the first position, corresponding to the FIG. 1 illustration, the reflected beam forms a low angle of incidence on the specimen surface. In the second mirror position 27', the reflected beam 46' forms a high angle of incidence with the specimen surface. The property of the ellipse which maintains the focusing conditions between the focal point 51' on the mirror 27 and the focal point 25 at the specimen preserves the optical alignment and focussing conditions for any selected incident angle so long as the beam 45 is incident on the ellipsoidal surface 22. The corresponding beam paths and optical alignment also takes place between the specimen 20, the second ellipsoidal mirror 23 and the second movable mirror 28. As is evident, with respect to a vertical plane perpendicular to the wall 12 and passing through the specimen focus 25, the optical system to the right of the specimen support 13 is a mirror image of that to the left.

By choosing ellipsoidal segments of sufficient length, an accessory has been constructed providing the ability to continuously vary the incident angle on the specimen from 5° to 85° without misaligning the system. This is an important feature of the invention, because spectra measured at different angles can be obtained under the same conditions and can be quantitatively compared. Furthermore, since changing the angle of incidence does not require repositioning the sample, the sample can easily be enclosed in a chamber with controlled conditions, such as temperature, pressure, and/or atmosphere.

In addition, in accordance with the invention, with changes in the incident angle, the focal point of the incident beam remains always on the sample and reflects from the same area of the sample. This minimizes the required sample area and also permits examination of samples with a moderate curvature. Furthermore, areas of special interest, such as contaminants or surface defects, may be isolated for analysis.

A further feature of the invention is that the polarization of the incident light does not vary with changes in the incident angle. This is important, since reflectance depends on the polarization of the incident light. In order to compare the experimental measurements to theoretical expressions, the polarization of the incident light must be known. This is easily achieved with the accessory of the invention.

Another important feature of the invention is its versatility and flexibility. The accessory can be used for a number of different reflection spectroscopy techniques requiring only minor alterations to the sample holder. To adapt the accessory for external reflectance, the sample is placed at the focal point 25. For internal reflectance, a hemispherical internal reflection element is mounted at the focal point 25 directly above and in contact with the horizontal sample. For diffuse reflectance, the sample is placed at the focal point 25 in or on a sampling cup which can be tilted or rotated. Although less of the reflected energy may be collected with this arrangement than with conventional accessories, the design of the accessory of the invention allows both variable angle and bidirectional diffuse reflection measurements.

Some applications taken with the accessory of the invention are illustrated in FIGS. 4–8. The results presented were obtained with a Mattsom Sirius 100 FT-IR spectrometer. For the internal reflection studies, the internal reflection element was a ZnSe hemisphere.

Figure 4:
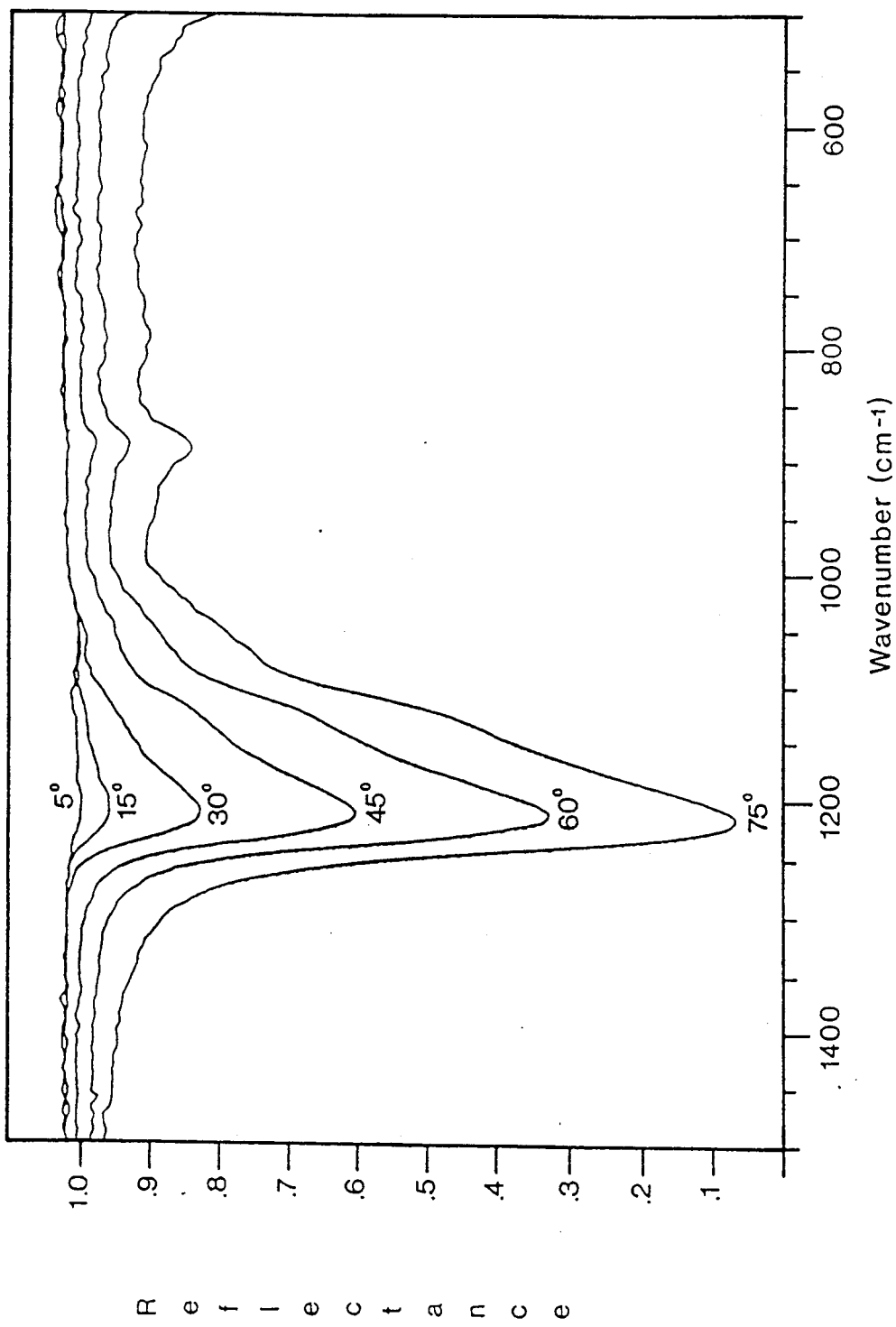
FIGS. 4-8 show spectra obtained with the accessory of the invention.
Figure 5:
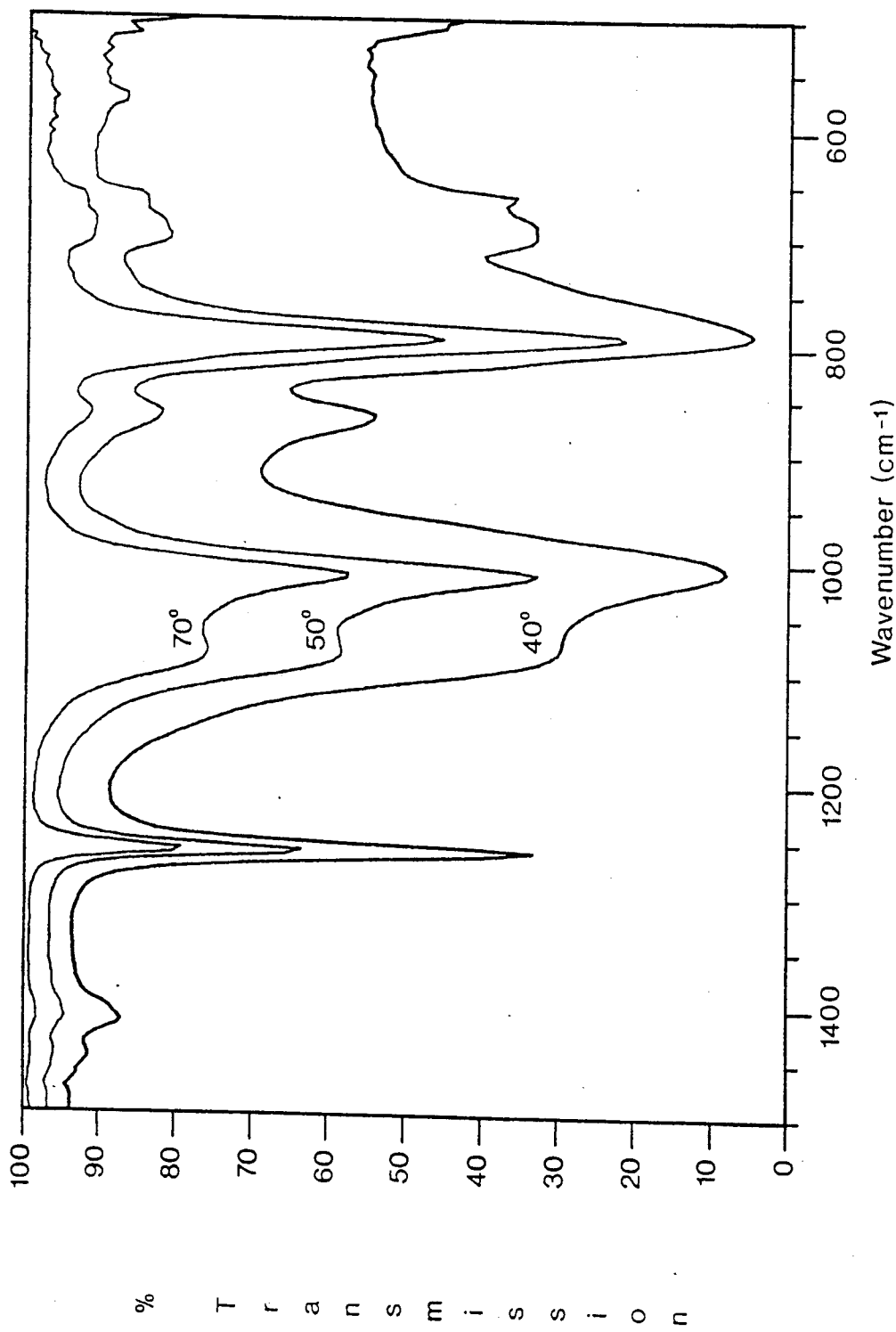

The advantage of being able to operate over a broad range of incident angles is illustrated by the spectra in FIG. 4 and 5. The former shows the external reflection spectra of a 0.05 μm thick $SiO_2$ film on an aluminum mirror and the latter shows the internal reflection spectra of RTV silicone. These spectra were recorded at incident angles from five to seventy-five degrees. Note that the spectral sensitivity depends strongly on incident angle, as expected.

Figure 6:
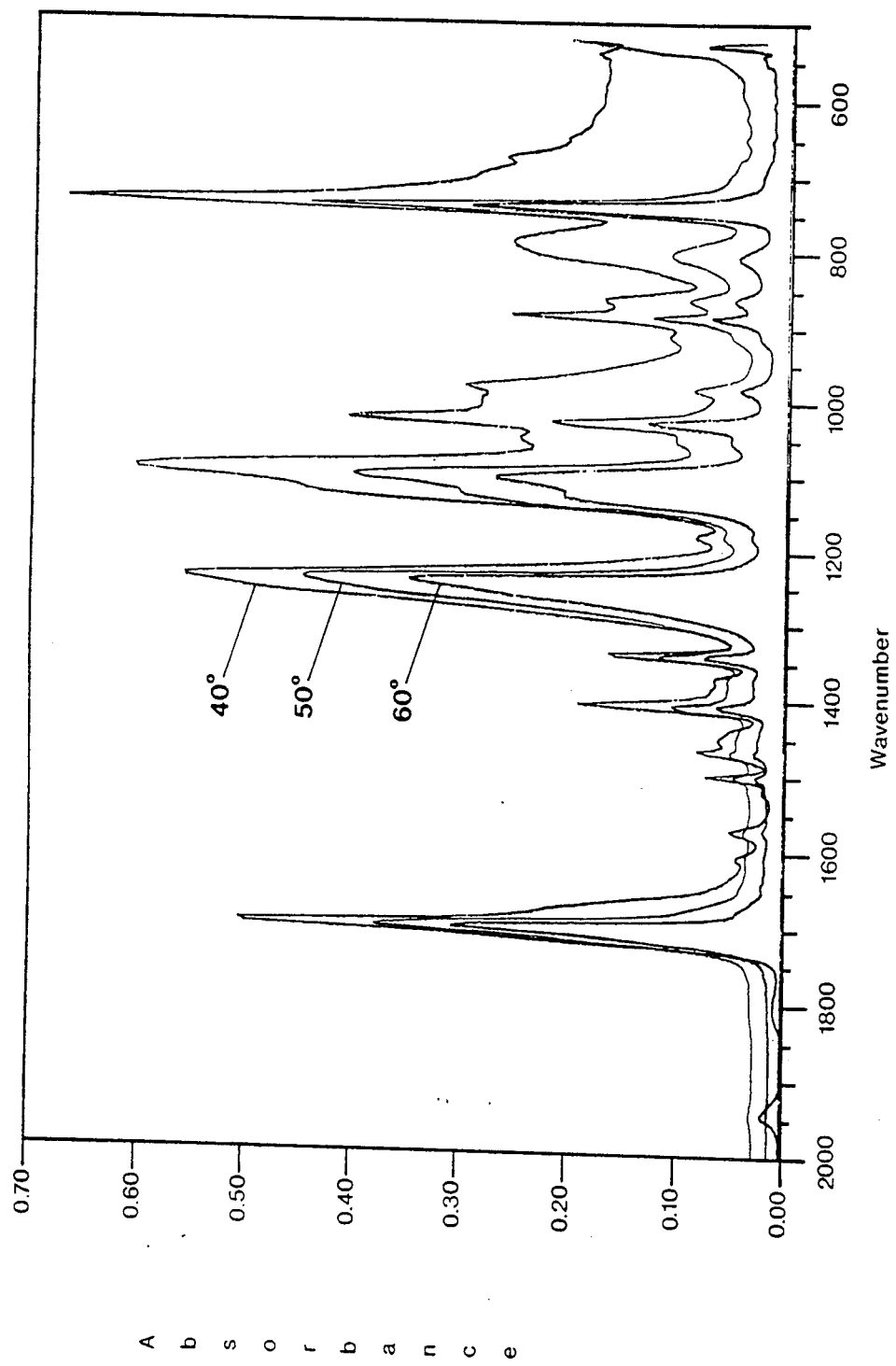

Variable angle reflection data can be used to determine sample thicknesses. FIG. 6 shows the internal reflectance of a 2.5 μm thick Mylar film over a silicone rubber substrate, measured with the accessory of the invention at a variety of incident angles. The silicone peak of 750–800 $cm^{-1}$ emerges from the Mylar spectrum as the incident angle decreases. Since different proportions of the surface layer relative to the substrate are probed at each incident angle, it is possible to deconvolute these spectra and determine the depth profile of the Mylar layer. Optical constants can also be determined with data acquired with the accessory of the invention.

Figure 7:
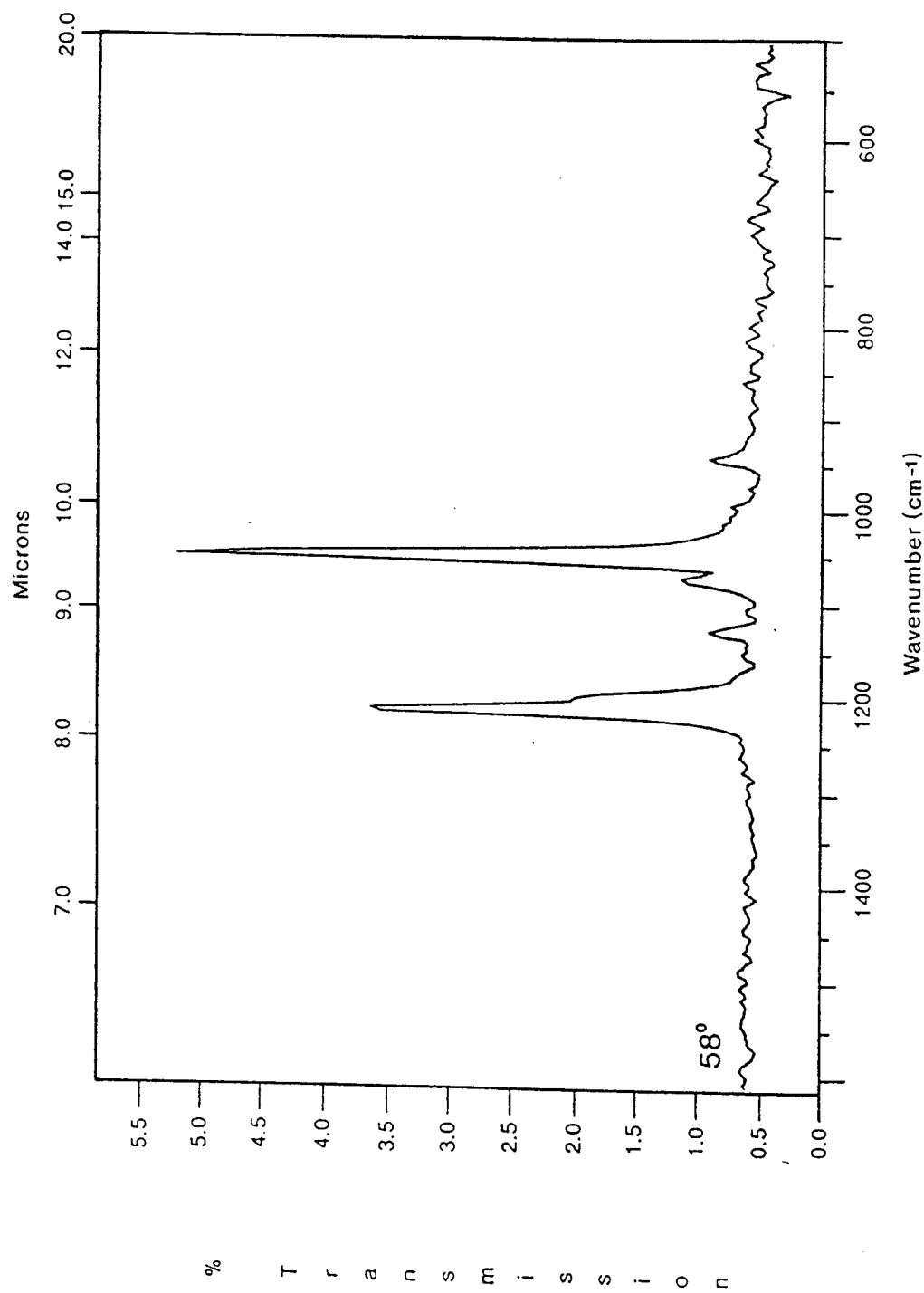

It is also possible to record variable angle reflection spectra from samples which are difficult to examine due to sample form or size. Liquid samples, for example, fall into this category since such samples are typically mounted vertically. In the accessory of the invention, however, the sampling surface is horizontal. This simplifies sample mounting. In addition to liquids, small samples pose problems in variable angle reflectance. Traditional variable angle reflection accessories do not probe the same area of the sample when the incident angle is varied. With small samples, recording spectra at various incident angles can require repositioning the sample for different incident angles. The accessory of the invention, however, always centers the incident radiation on the same sample area, eliminating the need to move the sample. FIG. 7 illustrates the external reflection spectra of a small sample, specifically a 12 mm diameter organometallic pellet at a 58° reflection angle. Equally good spectra were obtained of the same sample at various incident angles without altering the position of the sample.

Figure 8:
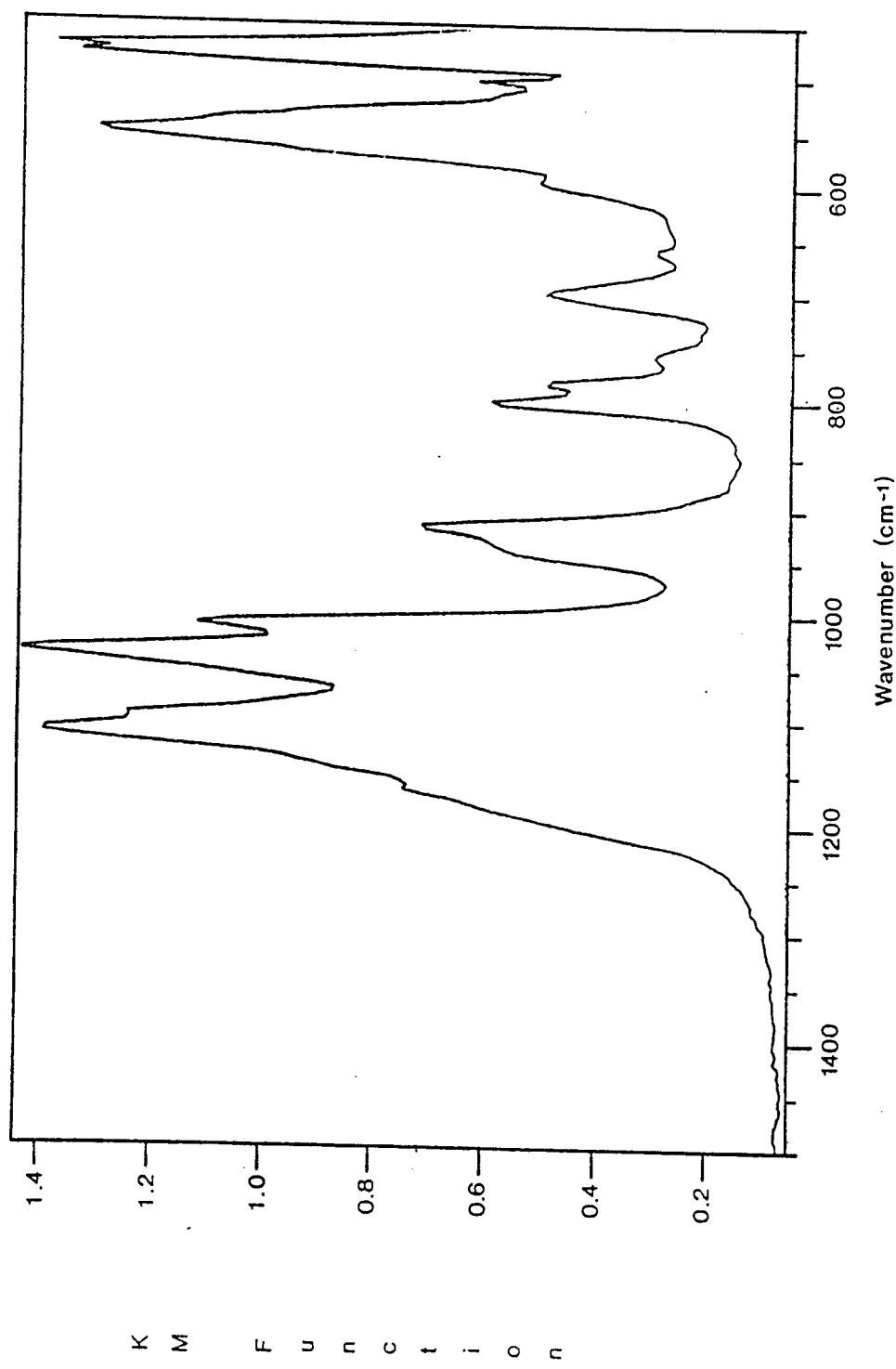

In addition to the uses of the accessory of the invention for external and internal reflectance, the accessory of the invention can also be adapted for diffuse reflection measurements. FIG. 8 shows the diffuse reflection spectrum of kaolinite powder diluted with KBr at a 15° reflection angle. This spectrum is similar to the diffuse reflection spectrum measured by conventional diffuse reflection equipment. Slight spectral differences are expected, since the accessary of the invention collects a different ratio of specular to diffuse reflectance than conventional accessories and this ratio can be changed by altering the incident angle.

In summary, a new variable angle reflection accessory has been described, which is versatile and which is easily reconfigured for the three different reflection techniques. It is useable over a large range of incident angles without requiring realignment or repositioning of the sample. Thus, this new accessory is a flexible and versatile addition to the field of reflection spectroscopy.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A variable angle reflection accessory for use in reflection spectrometry, comprising:
   means for supporting a sample having a surface to receive a radiation beam,
   first and second ellipsoidal segment reflectors mounted over the sample surface and in positions at first and second sides of the sample surface such that each ellipsoidal segment defines a first focus substantially at the sample surface and a second focus at, respectively, the first and second sides,
   first and second plane reflectors positioned, respectively, at the first and second sides with its reflecting surface at the location, respectively, of the second focus,
   optical means for directing a converging beam of radiation to the first plane reflector and for directing a diverging radiation beam from the second plane reflector,
   means for rotating the first and second plane reflectors in unison thereby to change the angle of incidence of the radiation beam on the sample surface.

2. A variable angle reflection accessory as claimed in claim 1, wherein the optical means for directing the converging beam of radiation comprises plane reflectors.

3. An accessory as claimed in claim 2, wherein the said optical means brings the converging radiation beam to a focus on the first plane reflector at the position of the said second focus of the first ellipsoidal reflector.

4. A variable angle reflection accessory as claimed in claim 3, wherein the optical means for directing the diverging beam is identical and a mirror image of the optical means for directing the converging beam.

5. The accessory of claim 4, wherein the optical means includes a first mirror and defines an optical path length to the first plane reflector, and said optical means includes a last mirror and defines the same optical path length from the second plane reflector, and the sum of said defined optical path lengths is substantially equal to the spacing between the first and last mirrors.

6. A variable angle reflection accessory for use in reflection spectrometry, comprising:

a support member, means for mounting on the support member a sample holder for a sample having a surface to reflect a radiation beam, first and second ellipsoidal segment reflectors fixedly mounted on the support member over the sample surface and in positions at the left and right sides of the sample surface such that each ellipsoidal segment defines a first focus substantially at the sample surface and a second focus at, respectively, the left and right sides of the sample surface, first and second plane reflectors on the support member and positioned, respectively, at the left and right sides each with its reflecting surface at the location, respectively, of the second focus of the first and second ellipsoidal reflectors, optical means for directing a converging beam of radiation from a spectrometer to a focus at the first plane reflector and for directing a diverging radiation beam from the second plane reflector back to the spectrometer, means for rotating the first and second plane reflectors in unison but in opposite directions so as to cause the radiation beam incident on the first plane reflector to scan across the surface of the first ellipsoidal segment whereby the beam reflected from the latter is incident on the sample surface at an angle of incidence that varies with the degree of rotation of the first plane reflector.

7. A variable angle reflection accessory as claimed in claim 6, wherein the optical means for bringing the radiation beam to the first plane reflector comprises at least one plane mirror for intersecting the radiation beam from the spectrometer.

8. A variable angle reflection accessory as claimed in claim 7, wherein the optical means for returning the beam to the spectrometer comprises at least one plane mirror, the spacing between said at least one plane mirrors being substantially equal to the sum of the optical path lengths between each of said one plane mirror and the first and second plane reflectors, respectively.

9. A variable angle reflection accessory as claimed in claim 8, wherein the ellipsoidal segment reflector and the plane reflector mounted on the support member to the left of the sample surface are the same as those mounted to the right but in mirror image positions.

10. A variable angle reflection accessory as claimed in claim 6, wherein the ellipsoidal segment reflectors and the plane reflectors are configured and positioned so as to allow the angle of incidence of the beam on the sample surface to be varied over the range of about 5°–85° without changing the said first and second focus.

11. A variable angle reflection accessory as claimed in claim 6, further comprising a scale for indicating the angle of incidence, and a pointer to said scale and connected to said means for rotating said first and second plane reflectors.

12. A variable angle reflection accessory as claimed in claim 11, wherein the scale is linear; and said means for rotating comprises a first lead screw connected to the pointer and operable by a user, a movable carriage connected to said first and second plane reflectors, a second lead screw connected to and operable to move said carriage, and means drivingly connecting said first and second lead screws.

13. A variable angle reflection accessory as claimed in claim 12, wherein the movable carriage is connected to each of the first and second plane reflectors by shafts having a common pivot point on the carriage.

14. A variable angle reflection accessory as claimed in claim 13, wherein the shafts are slideably connected to each of the first and second plane reflectors.

15. A variable angle reflection accessory as claimed in claim 6, wherein said means for rotating includes a mechanism coupling together the first and second plane reflectors.

16. A variable angle reflection accessory as claimed in claim 6, wherein the sample holder is fixed in position, and the radiation beam impinges directly on the sample surface.

* * * * *